US 6,630,666 B2

(12) United States Patent
Greaves

(10) Patent No.: US 6,630,666 B2
(45) Date of Patent: Oct. 7, 2003

(54) POSITRON TRAP BEAM SOURCE FOR POSITRON MICROBEAM PRODUCTION

(76) Inventor: Roderick G. Greaves, 344 Via Colinas, Thousand Oaks, CA (US) 91362

(*) Notice: Subject to any disclaimer, the term of this patent is extended or adjusted under 35 U.S.C. 154(b) by 0 days.

(21) Appl. No.: 09/912,372

(22) Filed: Jul. 26, 2001

(65) Prior Publication Data

US 2002/0030160 A1 Mar. 14, 2002

Related U.S. Application Data

(60) Provisional application No. 60/222,309, filed on Aug. 1, 2000.

(51) Int. Cl.⁷ .............................. G01N 23/00; G21K 7/00
(52) U.S. Cl. .......................... 250/308; 250/309
(58) Field of Search ............................ 250/308, 309

(56) References Cited

U.S. PATENT DOCUMENTS 5,159,195 A * 10/1992 Van House ................. 250/309
6,414,331 B1 * 7/2002 Smith et al. ............. 260/493.1

* cited by examiner

Primary Examiner—Jack Berman
Assistant Examiner—Alfred Dudding
(74) Attorney, Agent, or Firm—Jack C. Munro

(57) ABSTRACT

A positron producing apparatus which includes a vacuum chamber with a source of positrons to be supplied into the vacuum chamber forming a positron cloud within a Penning Trap. The positron cloud is to be compressed producing a thin positron beam which is extracted from the cloud and is smaller in cross-sectional area than the cloud. The positron beam is to be transmitted to a focusing apparatus which transmits the positron beam onto a solid target. The vacuum chamber is to include a cooling gas to be supplied into the vacuum chamber and a compressing device for the positron cloud is to include a rotating electric field. A method for compressing the positron cloud to produce a thin positron beam, which is to be transmitted to a solid for the purpose of analyzing properties of the solid, comprises the steps of supplying a source of positrons within a vacuum environment, forming and containing the positron cloud within a Penning Trap, producing a positron beam, and focusing of that positron beam onto a solid. The method is also to include adding of a cooling gas within the vacuum environment.

11 Claims, 2 Drawing Sheets

POSITRON TRAP BEAM SOURCE FOR POSITRON MICROBEAM PRODUCTION

This application claims the benefit of Provisional application Ser. No. 60/222,309, filed Aug. 1, 2000.

GOVERNMENT CONTRACT INFORMATION

This invention was made with U.S. Government support under Contract No. N00014-00-C-0710 awarded by the Office of Naval Research. The Government has certain rights in this invention.

BACKGROUND OF THE INVENTION

1. Field of the Invention

The field of this invention relates to devices for analyzing solids and more particularly to a device for analyzing a solid which uses positrons and the transmitting of those positrons onto the solid that is to be analyzed to result in the obtaining of information about the solid.

2. Description of the Related Art

A positron is an elementary particle with a mass equal to that of an electron and a positive charge equal in magnitude to the negative charge of an electron. The positron is thus the anti-particle of the electron. The positron has the same spin and statistics as the electron. A positron, is, in itself, stable but cannot exist indefinitely in the presence of matter, for it will ultimately collide with an electron. The positron and the electron will be annihilated as a result of the collision, and photons (gamma rays) will be created.

When a positron is injected into a solid substance, the positron will annihilate an electron and release gamma rays. These gamma rays are easily detected and can be used to measure properties of the solid material. Particles which can be released from the solid can also be used to measure properties of the solid material. These phenomena are the basis of a wide variety of techniques that can be used as tools for materials and surface analysis and can provide information that is not available from any other technique. Implementation of these techniques requires high quality positron beams. Currently, these techniques are being used at university laboratories, where the required positron beam systems are constructed by the users. However, such systems have the potential to be employed for industrial applications, such as quality control on integrated circuit production lines. It is this need that the current inventor is seeking to address by designing the subject matter of the present invention.

An important application of positron beams is a wide variety of techniques that have been developed for the analysis of solids and surfaces. Each of these techniques has its own characteristic positron beam requirements. Some employ steady state beams while others require pulsed beams. Several will provide usable data with relatively large diameter beams that are typical of radioactive positron source diameters (several millimeters) while other are applicable only using microbeams (less than ten microns in diameter).

In addition to surface analysis techniques, positrons can also be used to analyze properties of solids below the surface of the solid. This unique feature of positron based techniques arises because it is possible to measure the annihilation gamma rays from high energy positrons, which can easily penetrate to the surface of the solid. By varying the energy of the incident positron over a range of a few kilo-electron volts to greater than one hundred kilo-electron volts, positrons can be implanted to varying depths, thus permitting depth profiling of the properties of the solid. The information is contained either in the lifetime of the positrons or in the shape of the gamma ray line, which is Doppler-broadened by the momentum of the annihilated electrons and thus provides information about the chemical environment of the annihilation site.

The following is a list of some of the current applications for positron beams:

1. Positron Remission Spectroscopy (PRS)—This technique is based on the phenomenon that positrons implanted near the surface of a solid can thermalize, that is come to the same temperature as the surface of the solid, and be reemitted. The energy of the reemitted positrons can be analyzed to yield information that is not available with conventional scanning electron microscopy. This PRS technique has the ability to distinguish non-uniform film thickness, varying crystal orientation, differences in concentrations of microscopic voids in the crystal structure, concentrations of adsorbed molecules and contaminant layers.

2. Positron Annihilation Induced Auger Electron Spectroscopy (PAES)—This technique is analogous to Electron Induced Auger Electron Spectroscopy (AES), except that the core hole, which leads to the ejection of the Auger electron, is created by positron annihilation rather than electron impact. For this technique, positrons are injected at low energy into the surface to be analyzed. The ejected electrons are analyzed in the usual way using an electron energy spectrometer, but the measurement is substantially simplified because of the absence of background high-energy secondary electrons.

3. Reemitted Positron Energy Loss Spectroscopy (REPELS)—In this process, low energy monoenergetic positrons bombard the surface to be studied, and those that are reflected are energy analyzed. Energy is lost by transfer to vibrational modes and electronic state transitions of the surface and surface absorbed molecules. By measuring the magnitude of the energy lost, information can be obtained about the chemical composition of the surface of the solid and of surface absorbed molecules.

4. Low-energy Positron Diffraction (LEPD)—For this technique, a crystalline sample is bombarded with low energy (0–300 electron volts) monoenergetic positrons. Because of the low energy, there is relatively little penetration into the solid, and some of the positrons are reflected producing spots on a phosphor screen. This information can be used to determine the crystal structure of a clean substrate or to analyze an adsorbed layer.

5. Positron Induced Ion Desorption Spectroscopy (PIIDS)—This relatively new technique uses positrons to eject ions from the surface of the solid and measures the time required for the ions to reach a detector. Hence, the mass of the ions can be determined. The rate at which the ions are ejected from the surface of the solid is much greater when positrons are used rather than photons.

6. Positron Annihilation Lifetime Spectroscopy (PALS)—Positrons injected into a surface can accumulate in microscopic voids of the solid where such will eventually annihilate an electron of the solid. For high energy positrons obtained directly from the radioisotope of sodium, sodium-22, the lifetime can be measured by recording the time delay between the 1.2 million electron volt gamma rays that are emitted by the sodium nucleus simultaneously with the positron and the 511 kilo-electron volt annihilation gamma rays. This technique has been extensively applied to the study of bulk properties of solids. One of the most important current applications of lifetime spectroscopy is the analysis of microvoids in semiconductors and polymers. This technique is the most sensitive one available for studying voids in solids and can provide information about both the size and concentration of the voids. The technique has been applied to characterizing the properties of semiconductors, such as ion-implanted silicon, to study, for example, stress voiding and electromigration. One of the most important current areas of research is the study of the properties of polymers. Positron lifetime spectroscopy is capable of measuring the size and distribution of voids, which determine properties such as strength of the solid, gas permeability of the solid and aging characteristics of the solid. Another important topic is the development of insulators with low dielectric constant for use in microelectronic fabrication. Such insulators are essential for increasing microprocessor speeds and the positron technique described can be used to measure the properties of these insulators.

7. Variable Energy Positron Lifetime Spectroscopy (VEPLS)—The power of the PALS technique can be substantially enhanced by implementing it using a positron beam source of constant energy rather than a radioactive source which has a range of energies. By varying the beam energy, positrons can be implanted to varying depths so that a depth profile of void size and concentration can be obtained. Furthermore, if the beam diameter is small, it can be scanned across the surface of the solid so that three dimensional information can be obtained. This three dimensional information is obtained by scanning the positron beam across the surface when the size of the beam is smaller than the characteristic features of the solid being examined, such as a transistor. This technique requires positron pulses that are shorter than the typical time it takes a positron to annihilate an electron in a solid.

8. Positron Annihilation Spectroscopy (PAS)—This technique measures the Doppler-broadening of the 511 kiloelectron volt gamma ray line resulting from the annihilation of positrons implanted into solids. The required information is contained in the gamma ray line shape. PAS can provide the same type of information about defects as PALS and VEPLS.

Of the techniques numerated above, PALS, PAS and VEPLS have the capability of providing information to the integrated circuit manufacturing industry that is not available from any other technique. All of the above techniques can be used to obtain information about surfaces and solids in two and three dimensions if such are applied using beams of small diameter (10 microns or less). Such beams can be scanned across a surface and the emitted particles or gamma rays analyzed at each position to create two-dimensional images of surface properties. Furthermore, if this procedure is repeated using positrons of different energies, three dimension images can be created that reveal sub-surface structures and properties.

Positron microbeams have been created using the technique called remoderation brightness enhancement. This method reduces the beam diameter by a factor of ten but has the unwanted side affect of reducing the beam intensity by seventy percent or more. Microbeams can be created from large diameter beams by repeating this process several times. The flux of the resulting beams are typically only a few percent of the incident beam. This means that long data acquisition times are required to obtain useful data. The present invention has addressed this problem by producing positron microbeams with much greater efficiency than is possible using remoderation brightness enhancement.

SUMMARY OF THE INVENTION

A positron beam producing apparatus which utilizes a vacuum chamber with a source of positrons within the vacuum chamber and the positrons forming a positron cloud. The apparatus is used to compress the positron cloud and to produce a thin positron beam which is extracted from the cloud. The positron beam is transmitted to a focusing device and from the focusing device to a target where gamma rays and particles are released which can be used to analyze the properties of the target.

The positron producing apparatus, as previously described, plus use of a cooling gas within the vacuum chamber.

The positron producing apparatus, as previously described, which further includes use of an electrostatic lens as the focusing device.

The positron producing apparatus, as previously described, which further includes a series of annular electrodes located axially through which the positrons are to be passed.

The positron producing apparatus, as previously described, which further includes use of a rotating electric field within the positron cloud compressing device.

The positron producing apparatus, as previously described, which further includes a series of Penning Traps as the positron cloud compressing device.

A method of compressing a positron cloud producing a thin positron beam which is to be transmitted onto the solid for the purpose of analyzing properties of the solid which comprises the steps of supplying a source of positrons within a vacuum environment, forming a positron cloud, subjecting the positron cloud to magnetic and electric fields to confine the positrons, subjecting the positron cloud to a rotating electric field to compress the cloud, extracting a positron beam from the cloud, focusing of the positron beam, and transmitting of the focused beam onto the solid.

A further method of compressing a positron cloud where the previously described method also adds a cooling gas into the vacuum environment.

The positron beam producing apparatus of the present invention is a versatile, high quality, positron beam source that can supply positrons for many of the analytical tools that have been used in the past and have been described in the Background of the Invention. The positron beam producing apparatus of the present invention is to provide commercial availability of a low cost, compact, user friendly positron beam source that is expected to be useful to a variety of users worldwide.

BRIEF DESCRIPTION OF THE DRAWINGS

For a better understanding of the present invention, reference is to be made to the accompanying drawings. It is to be understood that the present invention is not limited to the precise arrangement shown in the drawings.

DETAILED DESCRIPTION OF THE INVENTION

Figure 1:
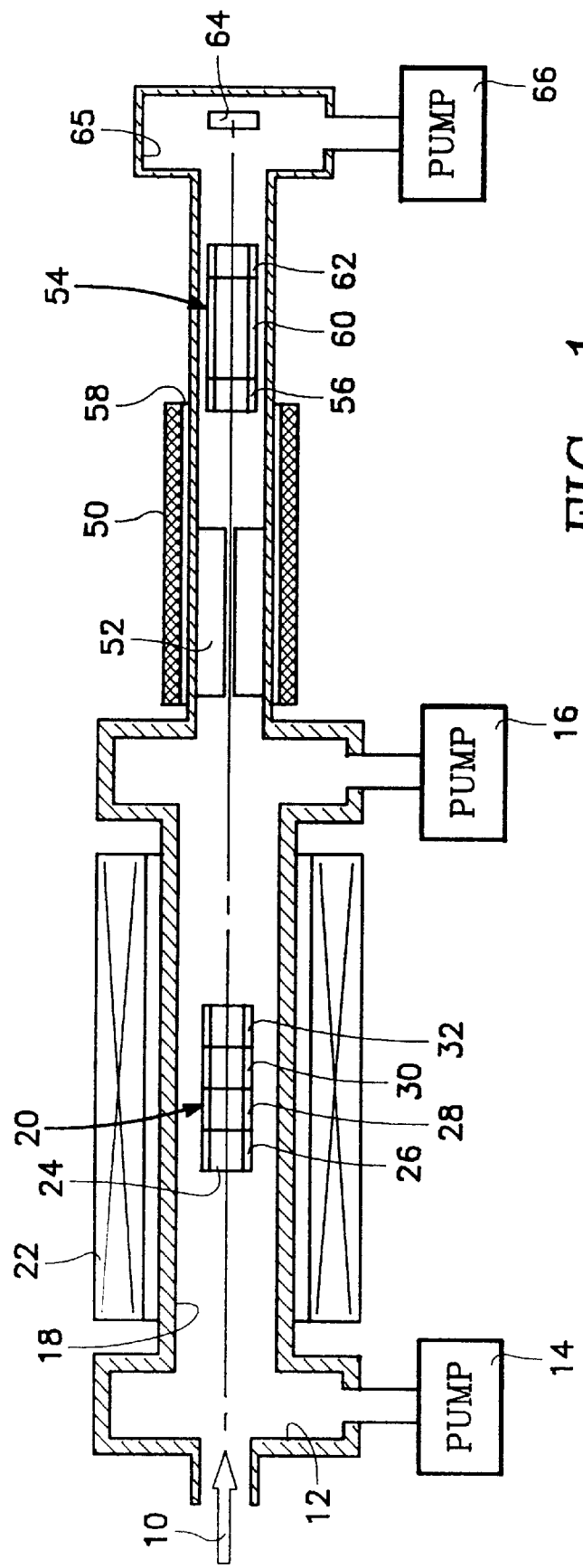
FIG. 1 is an overall schematic view of the positron producing apparatus of the present invention.

FIG. 1 shows the overall schematic view of the positron trap beam source of the present invention. A quantity of positrons is to be supplied from a source (not shown) in the direction of arrow 10 to within a vacuum chamber 12. The positrons 10 could be provided from a short pulse linear accelerator or other suitable positron source. The vacuum within the vacuum chamber 12 is supplied by a vacuum pump 14 and a vacuum pump 16. The vacuum chamber 12 includes a center section 18. The positrons 10 are to be directed in through the center section 18.

Figure 2:
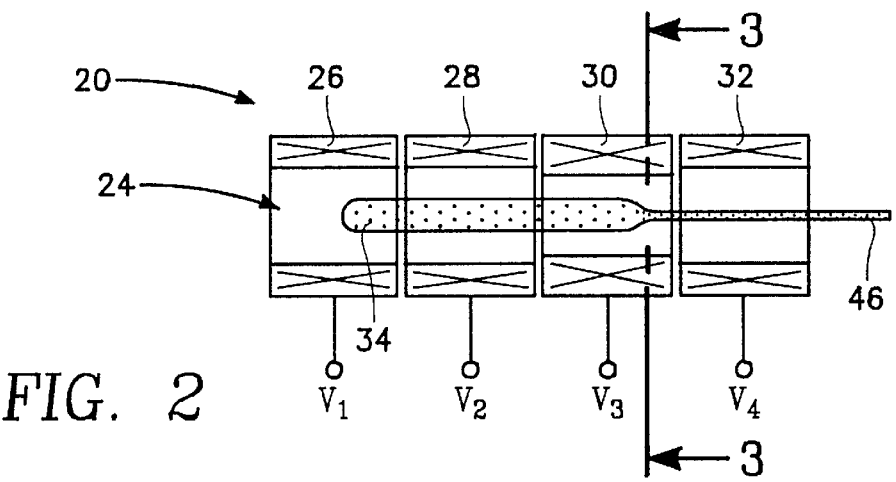
FIG. 2 is a longitudinal cross-sectional view of the compression trap (Penning Trap) of the present invention showing the extraction of the positron beam from the positron cloud.

Within the center section 18 of the vacuum chamber 12 is located a positron compression trap 20. The positrons 10 are radially confined by a solenoid magnet 22 which surrounds the center section 18. The confined positrons 10 are then supplied within the through opening 24 of the compression trap 20. The positrons 10 within the through opening 24 initially form a positron cloud 34 (see FIG. 2). This positron cloud 34 is typically greater than one millimeter in diameter. The through opening 24 is formed by an in-line series of ring shaped electrodes 26, 28, 30 and 32. The compression trap 20 receives the positrons 10 from the source and collects such within the through opening 24 of the compression trap 20.

The electrodes 26, 28, 30 and 32 are immersed in the magnetic field created by the solenoid magnet 22. Although, in referring to FIG. 2, the compression trap 20 is shown to include four in number of electrodes 26, 28, 30 and 32, it is considered to be within the scope of this invention that this number of electrodes could be increased or decreased without departing from the scope of this invention.

The electric field produced by the electrodes 26, 28, 30 and 32 causes axial confinement of the positrons 10 producing the positron cloud 34 within the confines of electrodes 26, 28, 30 and 32. Electrode 26 has voltage $V_1$, electrode 28 has voltage $V_2$, electrode 30 has voltage $V_3$, and electrode 32 has a voltage $V_4$. The voltages $V_1$, $V_2$, $V_3$ and $V_4$ are selected to provide axial confinement of the positron cloud 34. This is achieved by biasing electrodes 26 and 32 positive relative to electrodes 28 and 30. The voltage must be suitable to confine the positrons 10. The potential energy associated with the voltage must be about a factor of ten greater than the thermal energy of the positrons which is one-fortieth of an electron volt for room temperature positrons. By way of example, voltages $V_1$ and $V_4$ could be ten volts, and voltages $V_2$ and $V_3$ could be zero volts. The configuration that provides a combination of radial magnetic confinement and axial electrostatic confinement is commonly referred to as cylindrical Penning Trap.

Figure 3:
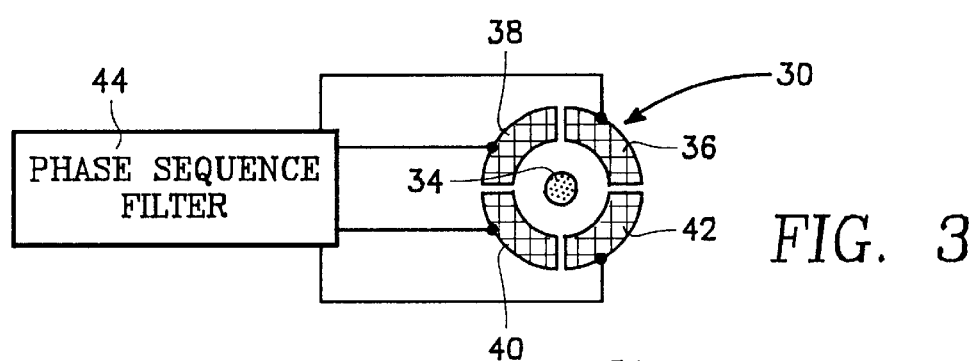
FIG. 3 is a cross-sectional view taken along 3—3 of FIG. 2 which shows the azimuthal segmentation of one of the confining electrodes and the phasing of the applied sine waves that are required to produce a rotating electric field.

The compression trap 20 also compresses the positron cloud 34 radially by applying a rotating electric field. This rotating electric field is created by applying suitably phased, sinusoidally time varying voltages to the electrode 30. Electrode 30 is divided azimuthally into four, equally spaced apart, electrically isolated segments 36, 38, 40 and 42. The construction of the electrode 30 is clearly shown in FIG. 3. Each of the segments 36, 38, 40 and 42 are basically ninety degree arcuate electrodes. The segments 36, 38, 40 and 42 are electrically connected to a phase sequence filter 44 or functionally similar device. The voltages applied to the segments 36, 38, 40 and 42 are sequentially shifted ninety degrees in phase such that an electric field is produced transverse to the magnetic axis, which is the longitudinal center axis through the Penning Trap 20, and rotating around the magnetic axis. The function of the rotating electric field is to compress radially the positron cloud 34 prior to the extraction of a positron beam 46. This positron beam 46 will generally be no more than one millimeter in diameter and substantially smaller in diameter than the positron cloud 34. When it is desired to transmit the beam 46, the voltage $V_4$ can be lowered which will permit the beam 46 to be transmitted to an electrostatic lens 54.

It is to be noted that cooling (loss of energy) of the positrons in the positron cloud 34 is required for this technique to work because the electric field around the positron cloud 34 has the unwanted side affect of producing positron heating, which leads to loss of positrons from the compression trap 20. Therefore, it is normally advisable to supply within the through opening 24 a small amount of a low pressure gas which is to function as a cooling mechanism. Cloud compression by a factor of 4.5 in diameter (leading to an increase by a factor of twenty in central density) was obtained using carbon tetrafloride or sulphur hexafloride gases at pressures as low as $1 \times 10^{-8}$ torr. At these pressures, the density of gas is so low that positron annihilation is negligible and, therefore, efficient usage of positrons is possible. It is expected that other gases can also be used to efficiently cool a compressed positron cloud. Higher compression factors are expected to be possible by using additional compression stages of different diameters where the down stream diameters are smaller. As a result, positron clouds with diameters of approximately 0.1 millimeters are expected to be achieved.

Once the positron cloud 34 has been compressed to the maximum degree possible, which is the point at which no further reduction of the radius occurs, the positron beam 46 is created with the beam 46 being released from the compression trap 20.

This is accomplished by reducing the voltage $V_4$. The voltage at the center of the positron cloud 34 is more positive than at the outer edge of the cloud 34 due to the space charge of the positrons. Thus, as the confining voltage ($V_4$) is reduced, positrons located nearest the longitudinal center axis of the cloud 34 will be released first in the form of the positron beam 46, that is, of course, narrower than the positron cloud 34. By continuing to apply the rotating electric field as positrons are released, it is possible to replenish the positrons that were previously released from the center of a cloud. Thus, it is possible to release all of the positrons in the form of a beam 46 that is much narrower than the original positron cloud 34 diameter.

Further reduction of the diameter of the positron beam 46 can be achieved by extracting the positron beam 46 from the magnetic field of the compression trap 20 and using conventional electrostatic lenses to focus the beam, such as electrostatic lens 54. It is to be noted that the electrostatic lens 54 is also located within the confines of the vacuum. The electrostatic lens 54 which is to focus the beam 46 may include a small diameter, solenoidal extraction magnet coil 50 which functions to extend the magnetic field of the compression trap 20. The positron beam 46 can also be conducted through a pumping restriction 52 to help isolate the vacuum environment within the compression trap 20 from that down stream of the pumping restriction 52, which is maintained by vacuum pump 66. From the pumping restriction 52, the positron beam 46 is supplied to electrostatic lens 54. It is noted that in FIGS. 4, 5 and 6 the pumping restriction 52 has been omitted for clarity. For the configuration shown in the drawings, the positron beam 46 is accelerated to about three kilo-electron volts by applying a voltage of minus three kilovolts to electrode 56 relative to electrode 32. The outer end 58 of the magnet 50 is positioned in alignment with the approximate mid-point of the electrode 56. This causes the magnetic field to decrease to zero rapidly from the fore end of the electrode 56 to the aft end of the electrode 56. The combination of the elevated positron energy and the short distance over which the magnetic field of extraction magnet coil 50 decreases to zero allows the positrons to be removed from the field without significant loss of positrons to the walls of the vacuum housing. The positrons then travel through electrodes 60 and 62 that have voltages applied so as to focus the positron beam 46 onto the target 64 at focal point 66. Target 64 is located within vacuum chamber 65 which is part of vacuum chamber 12. The focusing action is achieved by the electrodes 56 and 62 being at the same voltage and by making the voltage of electrode 60, some substantially different voltage than the voltage of electrodes 56 and 62 thereby forming a conventional electrostatic lens 54. Additional electrodes can be used to provide greater control over the focal properties of beam 46 if desired.

Figure 4:
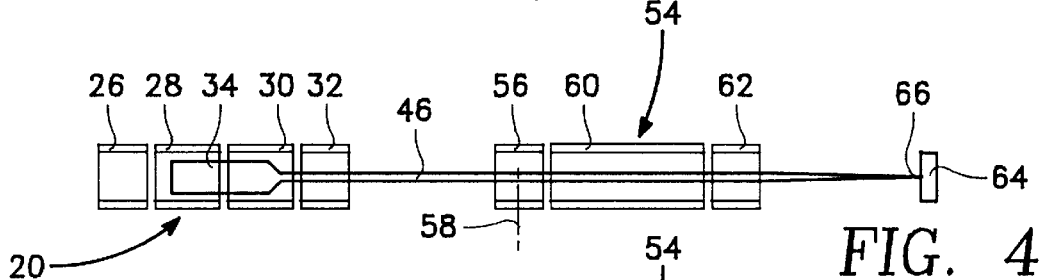
FIG. 4 is a schematic view that provides for accurate focusing of a positron beam that is being supplied from a Penning Trap. This figure shows the focusing of the positrons initially released from the center of the positron cloud.
Figure 5:
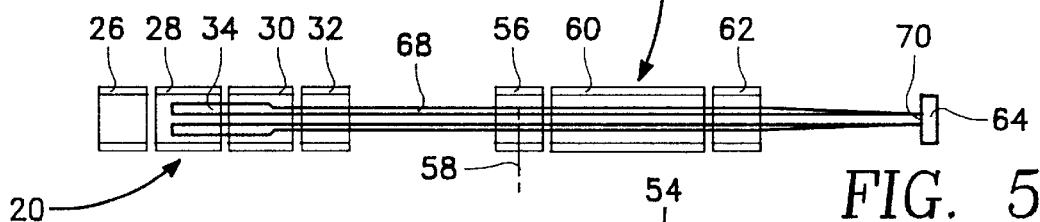
FIG. 5 is a view similar to FIG. 4 but shows how positrons are released from the Penning Trap with the positrons being out of focus.
Figure 6:
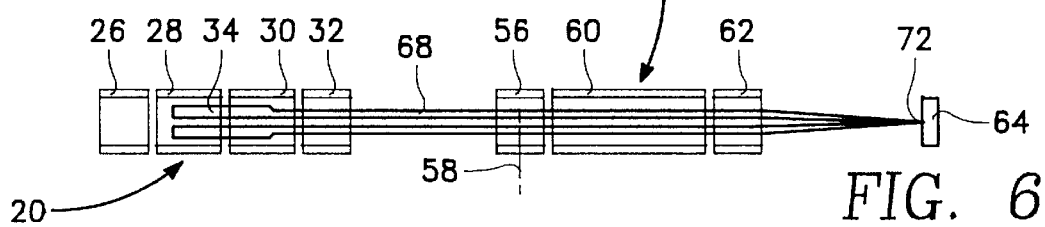
FIG. 6 is a view similar to FIG. 5 but shows how the out of focus positrons in the positron beam of FIG. 5 can be focused by adjusting of the voltages of the electrodes of the electrostatic lens.

An alternate method of reducing the diameter of the beam 46 following the compression of the positron cloud 34 is illustrated in FIGS. 5 and 6. For this procedure, the positrons are released in a continuous stream from the compression trap 20 by steadily reducing the confining voltage sufficiently rapidly that positrons cannot significantly change their radial location within the positron cloud 34 during the time of the extraction process. The rotating electric field is switched off during the extraction procedure. The positrons are initially released from the center of the cloud 34, as shown in FIG. 4, in the form of a narrow beam 46. This beam 46 is then extracted from the magnetic field and focused using the extraction optics 54. The voltages on the electrodes 56, 60 and 62 are initially adjusted to be optimum for positrons released from the center of the cloud 34, as shown in FIG. 4. However, because of aberrations of the electrostatic lens 54, these voltage settings will result in a poor focus for positrons subsequently released from larger radii, as illustrated in FIG. 5. In essence, the positrons are emitted from the positron cloud 34 in an annular beam pattern 68. If the voltages on the electrodes 56, 60 and 62 are maintained the same in FIG. 5 as in FIG. 4, this annular beam pattern 68 will result in a ring focus 70 on the target 64 rather than a point focus 66 of FIG. 4. In order to achieve the point focus, this deficiency can be corrected by continuously varying the voltages on one or more of the electrodes 56, 60 and 62, that is increasing the voltage on electrode 60 or decreasing the voltage on electrode 60. These voltages are to compensate for the increasing diameter of the annular positron beam 68. The required voltages can be calculated theoretically or measured experimentally. The result will be that the positrons will be focused onto a single spot 72 which is essentially identical to the focal point 66. This spot focusing of the annular positron beam 68 is shown in FIG. 6.

What is claimed is:

1. A positron beam producing apparatus comprising:

a vacuum chamber;

a source of positrons contained in said vacuum chamber, means for forming and containing a positron cloud;

means for compressing of said positron cloud using a rotating electric field;

means for extracting a thin positron beam which is emitted from said cloud and is smaller in cross-sectional area than said cloud;

means for focusing of said positron beam to a small area;

transmitting of said positron beam to said means for focusing; and transmitting of said positron beam onto a target with said small area contacting the target, whereby the interaction of the positrons with said target causes gamma rays and/or particles to be emitted which can be used to provide certain information for analyzing properties of the target.

2. The positron beam producing apparatus as defined in claim 1 wherein:

said means for compressing comprises a series of annular electrodes located axially each of which having a through opening through which said positrons are to be passed.

3. The positron beam producing apparatus as defined in claim 2 wherein:

one of said series of said annular electrodes comprising an azimuthal array of electrode segments, said azimuthal array of electrode segments are subjected to sequential activation producing said rotating electric field.

4. A positron beam producing apparatus comprising:

a vacuum chamber;

a source of positrons contained in said vacuum chamber, means for forming and containing a positron cloud;

means for compressing of said positron cloud;

means for extracting a thin positron beam which is emitted from said cloud and is smaller in cross-sectional area than said cloud;

means for focusing of said positron beam to a small area;

transmitting of said positron beam to said means for focusing;

transmitting of said positron beam onto a target with said small area contacting the target, whereby the interaction of the positrons with said target causes gamma rays and/or particles to be emitted which can be used to provide certain information for analyzing properties of the target; and said vacuum chamber contains a quantity of a gas to cool the positrons.

5. A positron beam producing apparatus comprising:

a vacuum chamber;

a source of positrons contained in said vacuum chamber, means for forming and containing a positron cloud;

means for compressing of said positron cloud;

means for extracting a thin positron beam which is emitted from said cloud and is smaller in cross-sectional area than said cloud;

means for focusing of said positron beam to a small area;

transmitting of said positron beam to said means for focusing;

transmitting of said positron beam onto a target with said small area contacting the target, whereby the interaction of the positrons with said target causes gamma rays and/or particles to be emitted which can be used to provide certain information for analyzing properties of the target; and said means for focusing comprising an electrostatic lens assembly, said electrostatic lens assembly includes an annular electromagnet which creates an axial magnetic field that terminates at an outer end, said outer end overlapping with an electrode of said electrostatic lens so that the magnetic field of said annular electromagnet decreases to zero rapidly within the length of said electrode.

6. A positron beam producing apparatus comprising:

a vacuum chamber;

a source of positrons contained in said vacuum chamber, means for forming and containing a positron cloud;

means for compressing of said positron cloud;

means for extracting a thin positron beam which is emitted from said cloud and is smaller in cross-sectional area than said cloud;

means for focusing of said positron beam to a small area;

transmitting of said positron beam to said means for focusing;

transmitting of said positron beam onto a target with said small area contacting the target, whereby the interaction of the positrons with said target causes gamma rays and/or particles to be emitted which can be used to provide certain information for analyzing properties of the target; and a vacuum pumping restriction is provided between the positron cloud and said means for focusing.

7. A positron beam producing apparatus comprising:

a vacuum chamber;

a source of positrons contained in said vacuum chamber, means for forming and containing a positron cloud;

means for compressing of said positron cloud;

means for extracting a thin positron beam which is emitted from said cloud and is smaller in cross-sectional area than said cloud;

means for focusing of said positron beam to a small area;

transmitting of said positron beam to said means for focusing;

transmitting of said positron beam onto a target with said small area contacting the target, whereby the interaction of the positrons with said target causes gamma rays and/or particles to be emitted which can be used to provide certain information for analyzing properties of the target; and the means for focusing of said positron beam is controlled to maintain a small beam area on the target as positrons are extracted from different radii within the positron cloud.

8. A method for compressing a positron cloud producing a thin positron beam which is to be transmitted to a solid for the purpose of analyzing properties of the solid comprising the steps of:

supplying a source of positrons within a vacuum environment;

forming and containing a positron cloud;

subjecting said positron cloud to a rotating electric field and a magnetic field to compress the positron cloud;

extracting a positron beam from said positron cloud;

focusing of said positron beam producing a focused beam; and transmitting of the focused beam onto said solid.

9. The method as defined in claim 8 wherein:

the subjecting step also includes the additional step of extracting a thin positron beam from said cloud wherein said positron beam is smaller in cross-sectional area than said cloud.

10. A method for compressing a positron cloud producing a thin positron beam which is to be transmitted to a solid for the purpose of analyzing properties of the solid comprising the steps of:

supplying a source of positrons within a vacuum environment;

forming and containing a positron cloud;

subjecting said positron cloud to electric and magnetic fields to compress the positron cloud;

extracting a positron beam from said positron cloud;

focusing of said positron beam producing a focused beam;

transmitting of the focused beam onto said solid; and adding a gas into the vacuum environment to cool the positrons.

11. A method for compressing a positron cloud producing a thin positron beam which is to be transmitted to a solid for the purpose of analyzing properties of the solid comprising the steps of:

supplying a source of positrons within a vacuum environment;

forming and containing a positron cloud;

subjecting said positron cloud to electric and magnetic fields to compress the positron cloud;

extracting a positron beam from said positron cloud;

focusing of said positron beam producing a focused beam;

transmitting of the focused beam onto said solid; and the focusing step includes using a vacuum pumping restriction prior to said focusing step.

* * * * *